United States Patent [19]

Preiss et al.

[11] Patent Number: 5,831,129
[45] Date of Patent: Nov. 3, 1998

[54] PREPARATION, WITH HETEROGENEOUS CATALYSIS, OF N-HYDROXYALKYL-SUBSTITUTED AMINOALKYNES

[75] Inventors: Thomas Preiss, Ludwigshafen; Jochem Henkelmann, Mannheim; Joachim Wulff-Döring, Frankenthal; Susanne Stutz, Weinheim; Thomas Rühl, Frankenthal, all of Germany

[73] Assignee: BASF Aktiengesellschaft, Ludwigshafen, Germany

[21] Appl. No.: 944,976

[22] Filed: Oct. 7, 1997

[30] Foreign Application Priority Data

Oct. 15, 1996 [DE] Germany .......... 196 42 553.0

[51] Int. Cl.⁶ .................................. C07C 209/02

[52] U.S. Cl. ............................ 564/487; 564/485

[58] Field of Search ...................... 564/487, 485

Primary Examiner—Brian M. Burn
Attorney, Agent, or Firm—Keil & Weinkauf

[57] ABSTRACT

N-Hydroxyalkyl-substituted aminoalkynes of the formula I

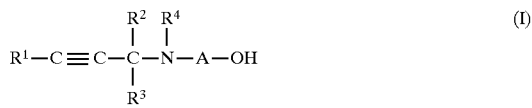

are prepared by reacting an alkyne with a 1-oxa-3-azaheterocyclo-alkane in a reaction with heterogeneous catalysis by a catalyst which comprises a compound of a metal of the first or second sub-group.

16 Claims, No Drawings

PREPARATION, WITH HETEROGENEOUS CATALYSIS, OF N-HYDROXYALKYL-SUBSTITUTED AMINOALKYNES

The present invention relates to a process, with heterogeneous catalysis, for preparing N-hydroxyalkyl-substituted aminoalkynes using a heterogeneous copper catalyst.

N-Hydroxyalkyl-substituted aminoalkynes are important industrial intermediates with many uses. Some of them are used as precursors for pharmaceuticals, but they are also employed in electroplating or as corrosion inhibitors.

The preparation of non-hydroxyalkyl-substituted aminoalkynes has been known for a long time and is used industrially. This generally entails appropriately substituted alkynes, carbonyl compounds and amines being reacted in a Mannich-type condensation with homogeneous or heterogeneous catalysis.

Processes of this type with homogeneous catalysis are widely used and have been described many times. Thus, for example, CH-A-669 192 describes the preparation of pharmacologically active N-arylalkyl-substituted aminoalkynes in a reaction with homogeneous catalysis by copper and zinc salts such as CuCl or $ZnCl_2$.

U.S. Pat. No. 3,496,232 describes the preparation of propargylamines from acetylene by a Mannich reaction. The catalysts described are salts of metals of the first or second subgroup, such as chlorides, acetates and formates of copper, which may also be supported. However, the reaction is preferably carried out by homogeneous catalysis with $CuCl_2$. The disadvantages of this process are that it must be carried out in an industrially elaborate manner with liquefied acetylene under high pressures (25 to 70 atm) and the yields of product are unsatisfactory.

A general problem in working with acetylene and homogeneous copper catalysts is that there is formation of catalytically active copper acetylides which are prone to explosive decomposition, can be removed from the reaction solution by filtration only with difficulty and, moreover, catalyze the formation of cuprene, a product of the polymerization of acetylene.

For easier manipulation of copper acetylides, they are applied to an inert carrier and mixed with a bismuth compound in order to reduce the formation of cuprene. However, the use of such known catalysts for aminoalkylation of alkynes which are gaseous under the reaction conditions requires high partial pressures in order to obtain an approximately acceptable space-time yield. On use of acetylene, which is a thermally unstable gas which easily explodes even under atmospheric pressure, considerable safety measures are necessary in the design of the reactors for the pressure ranges required, which makes these processes economically disadvantageous.

Thus, for example, EP A-0 080 794 describes a process with heterogeneous catalysis for preparing N,N-di-(alkyl, phenyl)-substituted propynylamines, employing as preferred catalysts copper acetylides on a magnesium silicate carrier which is doped with bismuth oxide. The reaction takes place, for example, in a stirred autoclave with a suspended catalyst or in a fixed bed. This process has the disadvantage that the supported catalyst used has unsatisfactory activity because of its low copper content (about 5 to 35%). Reaction of acetylene in this case requires partial pressures of up to 20 atm or more.

U.S. Pat. No. 3,650,985 describes the preparation of unsupported copper acetylide catalysts of the general formula $(CuC_2)_w (CH_2O)_x (C_2H_2)_y (H_2O)_z$ with $1 \leq w$, x, y<100, preferably w=4, x=0.24 to 4, y=0.24 to 4 and z=0.67 to 2.8. These catalysts may additionally contain a bismuth compound and can be prepared by formaldehyde and acetylene simultaneously acting on a particulate, water-insoluble copper compound, preferably basic copper carbonate, such as synthetic malachite. They are used as aqueous suspension of catalysts for the ethynylation of acetylenic hydrocarbons. Similar malachite catalysts are described in U.S. Pat. No. 3,560,576.

U.S. Pat. No. 4,127,734 describes the preparation of bismuth-modified, spherical malachites and their reaction with acetylene and formaldehyde to give unsupported ethynylation catalysts.

However, neither U.S. Pat. No. 3,650,985 nor U.S. Pat. No. 4,127,734 proposes the use of these specific catalysts in other reactions. In particular, there is no reference whatsoever to the possibility of using these catalysts for preparing aminoalkynes in nonaqueous medium.

Moreover, the skilled worker finds no reference in any of the publications discussed above to the preparation of hydroxyalkyl-substituted and, specifically, N-hydroxyalkyl-substituted amino-alkynes.

DE-A 26 37 425 describes the preparation of dialkylamino-2-alkyn-4-ols by reacting formaldehyde, dialkylamine and an alkynol in a Mannich-type condensation. However, in order to obtain satisfactory yields, it is necessary to comply with specific process conditions: it is necessary to use in an acidic solution, preferably at pH 5, a specific catalyst system, namely a combination of bromides, iodides or iodine, which are soluble in the reaction mixture, and soluble Cu(II) compounds. Carrying out the reaction with heterogeneous catalysis in a neutral or alkaline pH range is not suggested to be a possible variant.

DE-B 1 100 617 likewise describes the preparation with homogeneous catalysis of dialkylamino-2-alkyn-4-ols by reacting formaldehyde, dialkylamine and an alkynol in acidic aqueous solution at pH 5–6 with homogeneous catalysis by copper sulfate, acetate, nitrate or chloride.

There is no reference to the preparation of N-hydroxyalkyl-substituted aminoalkynes in either of the two last-mentioned publications.

GB-A 839 289 describes acetylenic ethanolamines and a process for preparing them. This is done by reacting an acetylene compound which has at least one active hydrogen atom with an oxazolidine of the following formula:

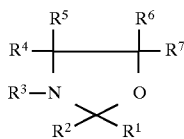

where $R^1$, $R^2$, $R^4$, $R^5$, $R^6$ and $R^7$ are identical or different and are hydrogen, alkyl, aryl, alkylaryl or arylalkyl, with the proviso that either $R^1$ or $R^2$ is hydrogen, and $R^3$ is alkyl, hydroxyalkyl, aryl, alkylaryl or arylalkyl.

The reaction takes place without solvent or in a suitable solvent, preferably dioxane or dimethylformamide, at from 0° to 30° C., under elevated or reduced pressure, preferably elevated pressure, in the presence or absence of an inert diluent gas. The catalysts used are homogeneous copper catalysts, eg. salts such as copper sulfate or copper chloride which dissociate in the reaction mixture and form a catalytically active complex with the acetylene. The catalyst is removed from the reaction mixture after completion of the reaction by first filtering off copper acetylide complexes which have precipitated, then precipitating the copper ions which are still present in the solution with hydrogen sulfide, and filtering off the resulting precipitate, with or without addition of active carbon. This procedure can no longer be carried out at acceptable expense with the safety standards now applying. As mentioned above, U.S. Pat. No. 3,496,233 describes the proneness of these copper acetylide complexes to explosive decomposition and the difficulty of removing them from the reaction solution by filtration. The precipitation with hydrogen sulfide, which is a flammable, highly toxic gas which has an unpleasant odor even in minute concentrations and, moreover, causes severe corrosion on metals, cannot now be implemented economically. The poorly soluble copper sulfides which are produced thereby would have to be either processed in a costly manner or disposed of as heavy metal waste. The filtration with the assistance of active carbon which is likewise described in the publication leads to a reduction in yield owing to adsorption of product.

CH-A 414 594 describes the preparation of N-hydroxyalkyl-substituted aminoalkines by reacting an oxazolidine or tetrahydro-1,3-oxazine with an acetylene compound in the presence of a source of copper ions and a solvent, preferably dioxane or dimethylformamide, at from 0° to 30° C. under a pressure from atmospheric to 40 cm Hg above atmospheric. In this case, only copper(I) chloride is used as homogeneous catalyst. The workup is entirely similar to the process described in GB-A 839 289 and consequently also has its disadvantages discussed above.

Shostakovskii et al. describe, in J. Org. Chem. USSR (Engl. Transl.), 6 (1970) 902 et seq. the preparation of N-hydroxyethyl-substituted aminopropynes by substitution of a radical in N,N-di-substituted aminoethanols with 3-bromopropyne in the presence of a base. An unwanted side reaction in this process is the enclosure of the precursors to form 2-vinyloxazolidines and other unsaturated compounds with a 1,4-oxazine framework so that the yields of product are only about 50% in some cases.

Kukharev et al. describe, in J. APPL. CHEM. USSR (Engl. Transl.) EN, 63, 8.2, (1990) 1736 et seq., the synthesis of N,N,N', N'-tetrakis(2-hydroxyethyl)-1,4-diamino-2-butyne by reacting N-(2-hydroxyethyl)oxazolidine with acetylene in the molar ratio 2:1 at from 19° to 24° C. in dioxane as solvent. Copper chloride is used as homogeneous catalyst. However, the maximum yield is only 45%, and the monocondensation product of oxazolidine with acetylene is also always obtained. The problems described above concerning the use of copper chloride as a homogeneous catalyst are likewise to be expected in this process.

It is an object of the present invention to provide a process for preparing N-hydroxyalkyl-substituted aminoalkynes which no longer has the disadvantages known in the prior art.

We have found that this object is achieved by a process in which an alkyne is reacted with a 1-oxa-3-azaheterocycloalkane in a reaction with heterogeneous catalysis by a catalyst which comprises a compound of a metal of the first or second subgroup. We have furthermore found, surprisingly, that the process according to the invention can be carried out under low pressures when an alkyne which is gaseous under the reaction conditions, such as acetylene, is used.

The present invention thus relates to a process for preparing N-hydroxyalkyl-substituted aminoalkynes of the general formula I

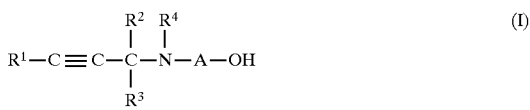

where

R$^1$ is hydrogen, alkyl, haloalkyl, cycloalkyl, aryl, alkoxy, alkoxyalkyl, hydroxyalkyl or

—CR$^2$R$^3$—NR$^4$—A—OH;

R$^2$ and R$^3$ are, independently of one another, hydrogen, alkyl, haloalkyl, cycloalkyl, aryl, alkoxy, alkoxyalkyl or hydroxyalkyl;

R$^4$ is hydrogen, alkyl, haloalkyl, cycloalkyl, aryl, alkoxy, alkoxyalkyl or hydroxyalkyl;

A is C$_2$–C$_5$-alkylene which is unsubstituted or substituted one or more times by alkyl, haloalkyl, aryl, alkoxy, hydroxyl and hydroxyalkyl;

which comprises reacting a mixture of an alkyne of the general formula II

where

R$^1$ has the abovementioned meanings, and a 1-oxa-3-azaheterocycloalkane of the general formula III

where

R$^2$, R$^3$, R$^4$ and A have the abovementioned meanings, in a reaction with heterogeneous catalysis using a catalyst which comprises a compound of a metal of the first or second subgroup.

For the purposes of the present invention, halogen is fluorine, chlorine, bromine and iodine and, in particular, chlorine and bromine.

The term "alkyl" comprises straight-chain and branched alkyl groups. These are preferably straight-chain or branched C$_{1-C12}$-alkyl and, in particular, C$_{1-C6}$-alkyl groups. Examples of alkyl groups are, in particular, methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl and dodecyl.

Haloalkyl is an alkyl group as defined above which is halogenated with one or more halogen atoms, in particular chlorine and bromine, partially or completely, preferably with one to three halogen atoms.

The above statements concerning the alkyl group apply correspondingly to the alkyl group in alkoxy, alkoxyalkyl and hydroxyalkyl radicals.

Cycloalkyl is preferably C$_{3-C8}$-cycloalkyl such as cyclopropyl, cyclobutyl, cyclopentyl, cyclohexyl, cycloheptyl or cyclooctyl, or cyclopentylmethyl, cyclopentylethyl and cyclohexylmethyl and cyclohexylethyl.

Aryl is preferably phenyl or naphthyl.

It is generally possible to use for the process according to the invention with heterogeneous catalysis the supported and unsupported catalysts also used for ethynylation reactions.

Supported catalysts of this type are known in the prior art and are described, for example, in U.S. Pat. No. 4,119,790 and EP-A 80 794, which are incorporated herein by reference.

Preferably used in the process according to the invention is a compound of a metal of the first or second subgroup of the Periodic Table on an inert carrier and, in particular, a supported copper acetylide catalyst which is prepared from a precursor which comprises 10–20% by weight of copper oxide, 1–5% by weight of bismuth oxide, and silica as carrier material. A copper acetylide which is particularly preferably used has been prepared from a precursor which comprises about 14–15% by weight of copper oxide, about 4% by weight of $Bi_2O_3$ and about 80% $SiO_2$.

Suitable unsupported catalysts comprise a copper acetylide complex and, in addition, a bismuth compound such as $(BiO)_2CO_3$, $Bi(NO_3)_3$ or $BiO(NO_3)$. Preferred catalysts contain about 40–70% by weight of Cu and about 0.1–10% by weight of Bi.

Catalysts of this type are also known in the prior art and are described, for example, in U.S. Pat. No. 3,650,985, U.S. Pat. No. 3,560,576 and U.S. Pat. No. 4,127,734. The disclosure in these publications is incorporated herein by reference.

In a preferred embodiment of the present invention, the catalyst used comprises at least one copper acetylide complex of the general formula IV

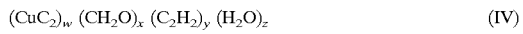

$(CuC_2)_w \cdot (CH_2O)_x \cdot (C_2H_2)_y \cdot (H_2O)_z$     (IV)

with $1 \leq w, x, y, z < 100$, and a bismuth compound.

The indices therein preferably have the following values:

w 2 to 6, in particular 4, x 0.24 to 4.00, y 0.24 to 2.40, z 0.67 to 2.8.

Processes for preparing these possibly Bi-doped copper acetylide complexes are likewise described in U.S. Pat. No. 3,650,985 and U.S. Pat. No. 4,127,734. The copper acetylide complexes used as unsupported heterogeneous catalysts according to the invention are generally obtained by simultaneous reaction of a copper compound selected from copper oxides, copper silicates, coppper phosphates, copper hydroxides and basic copper carbonates, such as natural and, preferably, synthetic malachites, in the presence of a bismuth compound selected from bismuth oxide carbonate and bismuth nitrate, in the presence or absence of an alkali metal carbonate or bicarbonate, with formaldehyde and acetylene.

The process according to the invention can be carried out in a stirred, tubular or loop reactor as a continuous or batchwise process. The reaction is generally carried out at from 0° to 200° C., preferably 20° to 150° C., in particular 40° to 120° C.

The pH of the reaction is set by the reactants and is in the neutral or alkaline pH range.

The reaction can be carried out without solvent or in the presence of an organic solvent which is inert toward the reactants. Examples of suitable solvents are saturated cyclic ethers such as tetrahydrofuran and dioxane.

In a preferred embodiment of the process according to the invention, alkynes of the formula II where $R^1$ is hydrogen, alkyl or hydroxyalkyl are reacted.

The process according to the invention is particularly suitable for reacting alkynes of the formula II which are gaseous at the particular reaction temperature, such as acetylene, propyne, 1-butyne etc. Acetlyene is preferably used.

If the compound of the formula II is acetylene, in a first variant of the process the 1-oxa-3-azaheterocycloalkane of the general formula III is introduced together with the catalyst, with or without a solvent, into an autoclave. Acetylene is injected until the initial pressure reaches about 2–8 bar, eg. about 5 bar, and the autoclave is subsequently heated to the reaction temperature. Then acetylene is again injected until a constant pressure of about 15–25 bar, eg. about 20 bar, is reached.

Reaction of alkynes which are gaseous under the reaction conditions advantageously takes place by a second variant of the process under a lower pressure than in prior art processes, namely under a pressure of up to 3 bar, preferably up to 2 bar and particularly preferably under ambient pressure.

If acetylene is used as alkyne of the formula II in the second variant of the process, it is preferably neither compressed nor liquefied for the reaction. The 1-oxa-3-azaheterocycloalkane of the formula III is introduced together with the catalyst, with or without a solvent, into a reactor provided with a mixing appliance. Suitable reactors are known to the skilled worker. They include the containers for reactions under pressure which are described in Ullmanns Enzyklopädie der technischen Chemie, 3rd Edition, Vol. 1, pages 117 et seq. and 769 et seq. (1951). The alkyne is preferably added below the level of the liquid reaction mixture, eg. using a dip pipe or a coiled pipe which has orifices facing in or against the direction of flow of the reaction mixture. The rate of addition is limited by the abovementioned pressure ranges which are to be maintained. One of the abovementioned unsupported heterogeneous catalysts is preferably used for the second variant of the process.

In a preferred embodiment, the compound of the formula III is a 1-oxa-3-azaheterocycloalkane of the formula IIIa or IIIb

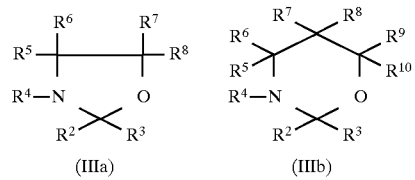

(IIIa)      (IIIb)

where $R^2$, $R^3$ and $R^4$ have the abovementioned meanings, $R^5$, $R^6$, $R^7$, $R^8$, R9 and $R^{10}$ are, independently of another, hydrogen, alkyl, haloalkyl, aryl, alkoxy, hydroxyl or hydroxyalkyl.

It is particularly preferred for $R^2$ and $R^3$ to be, independently, hydrogen or alkyl. $R^2$ and $R^3$ are particularly preferably both hydrogen.

$R^4$ is preferably hydrogen, alkyl or hydroxyalkyl.

In a preferred embodiment, $R^5$, $R^6$, $R^7$, $R^8$, $R^9$ and $R^{10}$ are, independently of another, hydrogen or alkyl. In this case, one, two or three of the radicals $R^5$, $R^6$, $R^7$, $R^8$, $R^9$ and $R^{10}$ are preferably alkyl.

Processes for preparing oxazolidines of the formula IIIa and tetrahydroxazines of the formula IIIb are known to the skilled worker. Thus, GB-A 839 289 describes the preparation of oxazolidines by condensing ethanolamine with an aldehyde or ketone.

CH-A 414 594 describes in a similar manner the synthesis of oxazolidines and tetrahydro-1,3-oxazines from unsubstituted or substituted ethanol- and propanolamines and the appropriate aldehydes. These publications are incorporated herein by reference.

The invention is illustrated by the following, non-limiting examples.

EXAMPLES

Example 1

Preparation of N-methyl-N-(2-hydroxypropyl)-3-aminopropyne ($R^1$, $R^2$, $R^3$=H; $R^4$=$CH_3$; A=—$CH_2$—CH($CH_3$)—)

10.1g (0.1 mol) of 3,5-dimethyloxazolidine were introduced into a 100 ml three-neck flask, and 50 ml of THF were added. Then 1.5 g of an acetylene-activated, unsupported copper catalyst (54% copper and 5% bismuth) were added to this solution, and acetylene was passed into the suspension, at 6 l/hour, at room temperature for 12 hours. Workup by distillation resulted in isolation of the monoadduct in 85% yield (based on heterocycle).

Example 2

Preparation of N,N-bis-(2-hydroxyethyl)-3-aminopropyne ($R^1$, $R^2$, $R^3$=H; $R^4$=$C_2H_4OH$; A=—($CH_2$)$_2$—)

5.85 g (0.05 mol) of N-hydroxyethyl-1,3-oxazolidine were introduced into a 60 ml autoclave, and 30 ml of THF were added. Then 5 g of an acetylene-activated supported copper catalyst (14–15% CuO, 4% $Bi_2O_3$, 80% $SiO_2$) were added to this solution. Subsequently 5 bar of acetylene were injected and the solution was heated to 50° C. Further acetylene was then injected until a constant pressure of 20 bar was reached. It was possible by workup by distillation to isolate N,N-dihydroxyethyl-3-aminopropyne in 80% yield (based on heterocycle). 18% N,N,N',N'-tetra(2-hydroxyethyl)-1,4-diamino-2-butyne were isolated as byproduct.

Example 3

Preparation of N-methyl-N-(3-hydroxypropyl)-3-aminopropyne ($R^1$, $R^2$, $R^3$=H; $R^4$=$CH_3$; A=—($CH_2$)$_3$—)

10.1 g (0.1 mol) of N-methyl-1,3-tetrahydrooxazine were introduced into a 50 ml two-neck flask, and 50 ml of THF were added. Then 1.5 g of an acetylene-activated unsupported copper catalyst (54% copper and 5% bismuth) were added to this solution, and then acetylene was passed into this suspension, at 6 l/hour, for 12 hours. Workup by distillation resulted in isolation of the monoadduct in 78% yield (based on heterocycle).

Example 4

Preparation of N,N-bis-(2-hydroxyethyl)-3-aminopropyne ($R^1$, $R^2$, $R^3$=H; $R^4$=$C_2H_4OH$; A=—($CH_2$)$_3$—)

11.7 g (0.1 mol) of N-hydroxyethyl-1,3-oxazolidine were introduced into a 100 ml three-neck flask, and 50 ml of THF were added. Then 1.5 g of an acetylene-activated, unsupported copper catalyst (54% copper and 5% bismuth) were added to this solution, and acetylene was passed into the suspension, at 6 l/hour, for 12 hours. Workup by distillation resulted in isolation of the monoadduct in 82% yield (based on heterocycle).

We claim:

1. A process for preparing N-hydroxyalkyl-substituted aminoalkynes of the general formula I

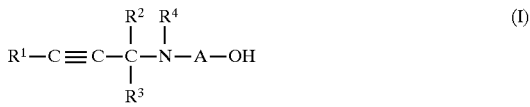

where $R^1$ is hydrogen, alkyl, haloalkyl, cycloalkyl, aryl, alkoxy, alkoxyalkyl, hydroxyalkyl or

$R^2$ and $R^3$ are, independently of one another, hydrogen, alkyl, haloalkyl, cycloalkyl, aryl, alkoxy, alkoxyalkyl or hydroxyalkyl;

$R^4$ is hydrogen, alkyl, haloalkyl, cycloalkyl, aryl, alkoxy, alkoxyalkyl or hydroxyalkyl;

A is $C_2$–$C_5$-alkylene which is unsubstituted or substituted one or more times by alkyl, haloalkyl, aryl, alkoxy, hydroxyl and hydroxyalkyl;

which comprises reacting a mixture of an alkyne of the general formula II

where $R^1$ has the abovementioned meanings, and a 1-oxa-3-azaheterocycloalkane of the general formula III

where $R^2$, $R^3$, $R^4$ and A have the abovementioned meanings, in a reaction with heterogeneous catalysis using a catalyst which comprises a compound of a metal of the first or second subgroup.

2. A process as claimed in claim 1, wherein the heterogeneous catalyst is a copper catalyst.

3. A process as claimed in claim 2, wherein the heterogeneous upper catalyst is an unsupported or supported catalyst.

4. A process as claimed in claim 3, wherein a bismuth-containing catalyst is used, the catalyst composition and/or the carrier being doped with bismuth.

5. A process as claimed in claim 4, wherein the catalyst composition comprises 40–70% by weight of copper and 0.1–10% by weight of bismuth.

6. A process as claimed in claim 1, wherein the copper catalyst is derived from malachite.

7. A process as claimed in claim 1, wherein a copper acetylide catalyst is used as copper catalyst.

8. A process as claimed in claim 7, wherein the catalyst comprises at least one copper acetylide complex of the general formula IV $(CuC_2)_w (CH_2O)_x (C_2H_2)_y (H_2O)_z$     (IV)

with $1 \leq w, x, y, z < 100$.

9. A process as claimed in claim 8, wherein a complex of the formula IV where w is from 2 to 6, x is from 0.24 to 4.00, y is from 0.24 to 2.40, and z is from 0.67 to 2.8, is used.

10. A process as claimed in claim 1, wherein an alkyne of the formula II where $R^1$ is hydrogen, alkyl or hydroxyalkyl is reacted.

11. A process as claimed in claim 10, wherein an alkyne which is gaseous at the reaction temperature is used as compound of the formula II.

12. A process as claimed in claim 11, wherein acetylene is used as compound of the formula II, and the reaction is carried out under a pressure of up to about 20 bar of acetylene.

13. A process as claimed in claim 1, wherein the compound of the formula III used is a 1-oxa-3-azaheterocycloalkane of the formula IIIa or IIIb

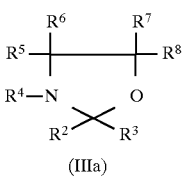 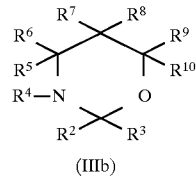

(IIIa)          (IIIb)

where $R^2$, $R^3$ and $R^4$ have the abovementioned meanings, $R^5$, $R^6$, $R^7$, $R^8$, $R^9$ and $R^{10}$ are, independently of one another, hydrogen, alkyl, haloalkyl, aryl, alkoxy, hydroxyl or hydroxyalkyl.

14. A process as claimed in claim 1, wherein the reaction is carried out at from 0° to 200° C., preferably 20° to 150° C., in particular 40° to 120° C.

15. A process as claimed in claim 1, wherein the reaction takes place in the neutral or alkaline pH range.

16. A process as claimed in claim 1, wherein the reaction takes place in a nonaqueous medium or without diluent.

* * * * *

UNITED STATES PATENT AND TRADEMARK OFFICE
CERTIFICATE OF CORRECTION

PATENT NO.: 5,831,129

DATED: November 3, 1998

INVENTOR(S): PREISS et al.

It is certified that error appears in the above-identified patent and that said Letters Patent is hereby corrected as shown below:

In the abstract, item [57], line 2 after the formula "azaheterocyclo-alkane" should be --azaheterocycloalkane--; last line, "sub-group" should be --subgroup--.

Col. 8, claim 1, line 26, "$c_2-c5$" should be --$c_2-c_5$--.

Col. 8, claim 3, line 53, "upper" should be --copper--.

Signed and Sealed this

Sixteenth Day of March, 1999

Q. TODD DICKINSON

*Attest:*

*Attesting Officer*     *Acting Commissioner of Patents and Trademarks*